United States Patent
Haderlein et al.

(10) Patent No.: US 7,700,795 B2
(45) Date of Patent: Apr. 20, 2010

(54) USE OF AZEOTROPICALLY DRIED NICKEL(II) HALOGENIDES

(75) Inventors: Gerd Haderlein, Grünstadt (DE); Robert Baumann, Mannheim (DE); Michael Bartsch, Neustadt (DE); Tim Jungkamp, Kapellen (BE); Hermann Luyken, Ludwigshafen (DE); Jens Scheidel, Hirschberg (DE); Heinz Schafer, Worms (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1007 days.

(21) Appl. No.: 10/577,130

(22) PCT Filed: Oct. 28, 2004

(86) PCT No.: PCT/EP2004/012174

§ 371 (c)(1),
(2), (4) Date: Apr. 25, 2006

(87) PCT Pub. No.: WO2005/042549

PCT Pub. Date: May 12, 2005

(65) Prior Publication Data

US 2007/0073071 A1 Mar. 29, 2007

(30) Foreign Application Priority Data

Oct. 30, 2003 (DE) ................ 103 51 022

(51) Int. Cl.
*C07F 15/04* (2006.01)
*C07F 9/50* (2006.01)
(52) U.S. Cl. ...................................................... 556/21
(58) Field of Classification Search .................... 556/21
See application file for complete search history.

(56) References Cited

U.S. PATENT DOCUMENTS

| 3,846,461 A | 11/1974 | Shook, Jr. |
| 3,903,120 A | 9/1975 | Shook, Jr. et al. |
| 5,523,453 A | 6/1996 | Breikss |
| 2003/0100442 A1 | 5/2003 | Chu et al. |

FOREIGN PATENT DOCUMENTS

| BE | 621207 | 2/1963 |
| DE | 1000477 | 8/1965 |
| EP | 0384392 | 8/1990 |
| GB | 882400 | * 11/1961 |

OTHER PUBLICATIONS

International Search Report No. PCT/EP2004/012174, dated Jan. 6, 2005, 2 pages.

* cited by examiner

*Primary Examiner*—Porfirio Nazario Gonzalez
(74) *Attorney, Agent, or Firm*—Connolly Bove Lodge & Hutz LLP

(57) ABSTRACT

A process is described for preparing a nickel(0)-phosphorus ligand complex containing at least one nickel(0) central atom and at least one phosphorus ligand, which comprises reducing a nickel(II) halide dried by azeotropic distillation in the presence of at least one phosphorus ligand.

10 Claims, No Drawings

USE OF AZEOTROPICALLY DRIED NICKEL(II) HALOGENIDES

CROSS REFERENCE TO RELATED APPLICATION

The present application is a National Stage application of PCT/EP2004/012174, filed Oct. 28, 2004, which claims priority from German Patent Application No. DE 103 51 002.8, filed Oct. 30, 2003.

The present invention relates to a process for preparing nickel(0)-phosphorus ligand complexes. The present invention further provides the mixtures which comprise nickel(0)-phosphorus ligand complexes and are obtainable by this process, and also relates to their use in the hydrocyanation of alkenes or isomerization of unsaturated nitriles.

Nickel complexes of phosphorus ligands are suitable catalysts for hydrocyanations of alkenes. For example, nickel complexes having monodentate phosphites are known which catalyze the hydrocyanation of butadiene to prepare a mixture of isomeric pentenenitriles. These catalysts are also suitable in a subsequent isomerization of the branched 2-methyl-3-butenenitrile to linear 3-pentenenitrile and the hydrocyanation of the 3-pentenenitrile to adiponitrile, an important intermediate in the preparation of nylon-6,6.

U.S. Pat. No. 3,903,120 describes the preparation of zerovalent nickel complexes having monodentate phosphite ligands starting from nickel powder. The phosphorus ligands have the general formula $PZ_3$ where Z is an alkyl, alkoxy or aryloxy group. In this process, finely divided elemental nickel is used. In addition, preference is given to carrying out the reaction in the presence of a nitrilic solvent and in the presence of an excess of ligand.

U.S. Pat. No. 3,846,461 describes a process for preparing zerovalent nickel complexes with triorganophosphite ligands by reacting triorganophosphite compounds with nickel chloride in the presence of a finely divided reducing agent which is more electropositive than nickel. The reaction according to U.S. Pat. No. 3,846,461 takes place in the presence of a promoter which is selected from the group consisting of $NH_3$, $NH_4X$, $Zn(NH_3)_2X_2$ and mixtures of $NH_4X$ and $ZnX_2$, where X is a halide.

New developments have shown that it is advantageous to use nickel complexes having chelate ligands (multidentate ligands) in the hydrocyanation of alkenes, since these allow both higher activities and higher selectivities to be achieved coupled with increased on-stream time. The above-described prior art processes are not suitable for preparing nickel complexes having chelate ligands. However, the prior art also discloses processes which enable the preparation of nickel complexes having chelate ligands.

U.S. Pat. No. 5,523,453 describes a process for preparing nickel-containing hydrocyanation catalysts which contain bidentate phosphorus ligands. These complexes are prepared starting from soluble nickel(0) complexes by transcomplexing with chelate ligands. The starting compounds used are $Ni(COD)_2$ or $(oTTP)_2Ni(C_2H_4)$ (COD=1,5-cyclooctadiene; oTTP=P(O-ortho-$C_6H_4CH_3$)$_3$). As a consequence of the complicated preparation of the starting nickel compounds, this process is expensive.

Alternatively, there is the possibility of preparing nickel(0) complexes starting from bivalent nickel compounds and chelate ligands by reduction. In this method, it is generally necessary to work at high temperatures, so that thermally unstable ligands in the complex in some cases decompose.

US 2003/0100442 A1 describes a process for preparing a nickel(0) chelate complex, in which nickel chloride is reduced in the presence of a chelate ligand and of a nitrilic solvent using a more electropositive metal than nickel, in particular zinc or iron. In order to achieve a high space-time yield, an excess of nickel is used which has to be removed again after the complexation. The process is generally carried out with aqueous nickel chloride, which may lead to its decomposition especially when hydrolyzable ligands are used. When operation is effected with anhydrous nickel chloride, especially when hydrolyzable ligands are used, it is essential according to US 2003/0100442 A1 that the nickel chloride is initially dried by a specific process in which very small particles having large surface area and therefore high reactivity are obtained. A particular disadvantage of the process is that this fine nickel chloride dust prepared by spray drying is carcinogenic. A further disadvantage of this process is that operation is generally effected at elevated reaction temperatures, which may lead to decomposition of the ligands or of the complex especially in the case of thermally unstable ligands. It is a further disadvantage that operation has to be effected with an excess of reagents, in order to achieve economically viable conversions. These excesses have to be removed in a costly and inconvenient manner on completion of the reaction and optionally recycled.

GB 1 000 477 and BE 621 207 relate to processes for preparing nickel(0) complexes by reducing nickel(II) compounds using phosphorus ligands.

It is an object of the present invention to provide a process for preparing nickel-phosphorus ligand complexes having phosphorus ligands which substantially avoids the above-described disadvantages of the prior art. In particular, an anhydrous nickel source should be used, so that hydrolyzable ligands are not decomposed during the complexation. In addition, the reaction conditions should be gentle, so that thermally unstable ligands and the resulting complexes do not decompose. In addition, the process according to the invention should preferably enable the use of only a slight excess, if any, of the reagents, so that there is, if at all possible, no need to remove these substances after the complex has been prepared. The process should also be suitable for preparing nickel(0) complexes having chelate ligands.

We have found that this object is achieved by a process for preparing nickel(0)-phosphorus ligand complexes which contain at least one nickel(0) central atom and at least one phosphorus ligand.

In the process according to the invention, an aqueous nickel (II) halide dried by azeotropic distillation is reduced in the presence of at least one phosphorus ligand.

Azeotropic Distillation

In the azeotropic distillation, an aqueous nickel(II) halide is used. Aqueous nickel(II) halide is a nickel halide which is selected from the group of nickel chloride, nickel bromide and nickel iodide and contains at least 2% by weight of water. Examples thereof are nickel chloride dihydrate, nickel chloride hexahydrate, an aqueous solution of nickel chloride, nickel bromide trihydrate, an aqueous solution of nickel bromide, nickel iodide hydrates or an aqueous solution of nickel iodide. In the case of nickel chloride, preference is given to using nickel chloride hexahydrate or an aqueous solution of nickel chloride. In the case of nickel bromide and nickel iodide, preference is given to using the aqueous solutions. Particular preference is given to using an aqueous solution of nickel chloride.

In the case of an aqueous solution, the concentration of the nickel(II) halide in water is not critical per se. An advantageous proportion of the nickel(II) halide in the total weight of nickel(II) halide and water has been found to be at least 0.01% by weight, preferably at least 0.1% by weight, more preferably at least 0.25% by weight, especially preferably at least 0.5% by weight. An advantageous proportion of the nickel(II) halide in the total weight of nickel(II) halide and water has been found to be in the region of at most 80% by weight, preferably at most 60% by weight, more preferably at most 40% by weight. For practical reasons, it is advantageous not to exceed a proportion of nickel halide in the mixture of nickel halide and water which results in a solution under the given temperature and pressure conditions. In the case of an aqueous solution of nickel chloride, it is therefore advantageous for practical reasons to select, at room temperature, a proportion of nickel halide in the total weight of nickel chloride and water of at most 31% % by weight. At higher temperatures, correspondingly higher concentrations can be selected and result from the solubility of nickel chloride in water.

The aqueous nickel(II) halide is dried before the reduction by azeotropic distillation. In a preferred embodiment of the present invention, the azeotropic distillation is a process for removing water from the corresponding aqueous nickel(II) halide, by admixing it with a diluent whose boiling point, in the case that the diluent mentioned does not form an azeotrope with water under the pressure conditions of the distillation mentioned below, is higher than the boiling point of water and is liquid at this boiling point of water, or which forms an azeotrope or heteroazeotrope with water under the pressure and temperature conditions of the distillation mentioned below, and distilling the mixture comprising the aqueous nickel(II) halide and the diluent to remove water or the azeotrope mentioned or the heteroazeotrope mentioned from this mixture to obtain an anhydrous mixture comprising nickel(II) halide and said diluent.

The starting mixture, in addition to the aqueous nickel(II) halide, may comprise further constituents such as ionic or nonionic, organic or inorganic compounds, especially those which are homogeneously and monophasically miscible with the starting mixture or are soluble in the starting mixture.

According to the invention, the aqueous nickel(II) halide is admixed with a diluent whose boiling point is higher than the boiling point of water under the pressure conditions of the distillation and which is in liquid form at this boiling point of water.

The pressure conditions for the subsequent distillation are not critical per se. Advantageous pressures have been found to be at least $10^{-4}$ MPa, preferably at least $10^{-3}$ MPa, especially at least $5\times10^{-3}$ MPa. Advantageous pressures have been found to be at most 1 MPa, preferably at most $5\times10^{-1}$ MPa, especially at most $1.5\times10^{-1}$ MPa.

Depending on the pressure conditions and the composition of the mixture to be distilled, the distillation temperature is then established. At this temperature, the diluent is preferably present in liquid form. In the context of the present invention, the term diluent refers either to a single diluent or to a mixture of such diluents, and, in the case of such a mixture, the physical properties specified in the present invention relate to this mixture.

In addition, the diluent, under these pressure and temperature conditions, preferably has a boiling point which, in the case that the diluent does not form an azeotrope with water, is higher than that of water, preferably by at least 5° C., especially at least 20° C., and preferably at most 200° C., especially at most 100° C.

In a preferred embodiment, diluents may be used which form an azeotrope or heteroazeotrope with water. The amount of diluent compared to the amount of water in the mixture is not critical per se. Advantageously, more liquid diluent should be used than corresponds to the amounts to be distilled off through the azeotropes, so that excess diluent remains as a bottom product.

Where a diluent is used which does not form an azeotrope with water, the amount of diluent compared to the amount of water in the mixture is not critical per se.

The diluent used is selected in particular from the group consisting of organic nitriles, aromatic hydrocarbons, aliphatic hydrocarbons and mixtures of the aforementioned solvents. With regard to the organic nitriles, preference is given to acetonitrile, propionitrile, n-butyronitrile, n-valeronitrile, cyanocyclopropane, acrylonitrile, crotonitrile, allyl cyanide, cis-2-pentenenitrile, trans-2-pentenenitrile, cis-3-pentenenitrile, trans-3-pentenenitrile, 4-pentenenitrile, 2-methyl-3-butenenitrile, Z-2-methyl-2-butenenitrile, E-2-methyl-2-butenenitrile, ethylsuccinonitrile, adiponitrile, methylglutaronitrile or mixtures thereof. With regard to the aromatic hydrocarbons, benzene, toluene, o-xylene, m-xylene, p-xylene or mixtures thereof may preferably be used. Aliphatic hydrocarbons may preferably be selected from the group of the linear or branched aliphatic hydrocarbons, more preferably from the group of the cycloaliphatics, such as cyclohexane or methylcyclohexane, or mixtures thereof. Particular preference is given to using cis-3-pentenenitrile, trans-3-pentenenitrile, adiponitrile, methylglutaronitrile or mixtures thereof as the solvent.

When the diluent used is an organic nitrile or a mixture comprising at least one organic nitrile, it has been found to be advantageous to select the amount of diluent in such a way that the proportion of the nickel(II) halide in the total weight of nickel(II) halide and diluent in the finished mixture is at least 0.05% by weight, preferably at least 0.5% by weight, more preferably at least 1% by weight.

When the diluent used is an organic nitrile or a mixture comprising at least one organic nitrile, it has been found to be advantageous to select the amount of diluent in such a way that the proportion of the nickel(II) halide in the total weight of nickel(II) halide and diluent in the finished mixture is at most 50% by weight, preferably at most 30% by weight, more preferably at most 20% by weight.

According to the invention, the mixture comprising the aqueous nickel(II) halide and the diluent is distilled to remove water from this mixture and obtain anhydrous mixture comprising nickel(II) halide and said diluent. In a preferred embodiment, the mixture is initially prepared and subsequently distilled. In another preferred embodiment, the aqueous nickel halide, more preferably the aqueous solution of the nickel halide, is added gradually to the boiling diluent during distillation. This allows the formation of a greasy solid, which is difficult to handle for a process technology point of view, to be substantially prevented.

In the case of pentenenitrile as a diluent, the distillation may advantageously be carried out at a pressure of at most 200 kPa, preferably at most 100 kPa, especially at most 50 kPa, more preferably at most 20 kPa.

In the case of pentenenitrile as a diluent, the distillation may preferably be carried out at a pressure of at least 1 kPa, preferably at least 5 kPa, more preferably 10 kPa.

The distillation may advantageously be effected by single-stage evaporation, preferably by fractional distillation, in one or more, such as 2 or 3, distillation apparatus. Useful apparatus for distillation is that which is customary for this purpose, as described, for example, in Kirk-Othmer, Encyclopedia of Chemical Technology, 3rd ed., Vol. 7, John Wiley & Sons, New York, 1979, page 870-881, such as sieve tray columns, bubble-cap tray columns, columns having structured or random packings, columns having a side draw or dividing wall columns.

The distillation may be effected batchwise.

The distillation may be effected continuously.

Ligands

In the process according to the invention for preparing nickel(0)-phosphorus ligand complexes containing at least one nickel(0) central atom and at least one phosphorus ligand, the nickel(II) halide dried by azeotropic distillation is reduced in the presence of at least one phosphorus ligand.

In the process according to the invention, the phosphorus ligands are preferably selected from the group consisting of phosphines, phosphites, phosphinites and phosphonites.

These phosphorus ligands preferably have the formula I $$P(X^1R^1)(X^2R^2)(X^3R^3) \quad (I)$$

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1 R^2 R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified below.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula Ia $$(\text{o-tolyl-O—})_w (\text{m-tolyl-O—})_x (\text{p-tolyl-O—})_y (\text{phenyl-O—})_z P \quad (Ia)$$

where w, x, y, z are each a natural number, and the following conditions apply: w+x+y+z=3 and w, z≦2.

Such compounds Ia are, for example, (p-tolyl-O-)(phenyl-O—)$_2$P, (m-tolyl-O-)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P (o-tolyl-O—)$_2$(m-tolyl-O—)P or mixtures of such compounds.

Mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained for example by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula Ib:

$$P(O—R^1)_x (O—R^2)_y (O—R^3)_z (O—R^4)_p \quad (Ib)$$

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$; aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y,z,p: each independently 0, 1 or 2, with the proviso that x+y+z+p=3.

Preferred phosphites of the formula Ib can be taken from DE-A 199 53 058. The $R^1$ radical may advantageously be o-tolyl, o-ethylphenyl, o-n-propylphenyl, o-isopropyl-phenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous R³ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The R⁴ radical is preferably phenyl. p is preferably zero. For the indices x, y and z and p in compound Ib, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula Ib are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula Ib are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula Ib may be obtained by
a) reacting a phosphorus trihalide with an alcohol selected from the group consisting of $R^1OH$, $R^2OH$, $R^3OH$ and $R^4OH$ or mixtures thereof to obtain a dihalophosphorous monoester,
b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and
c) reacting the monohalophosphorous diester mentioned with an alcohol selected from the group consisting of $R^1OH$, $R^2OH$, $R^3OH$ and $R^4OH$ or mixtures thereof to obtain a phosphite of the formula Ib.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to PCl₃. Further details on the reaction conditions in the preparation of the phosphites Ib and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

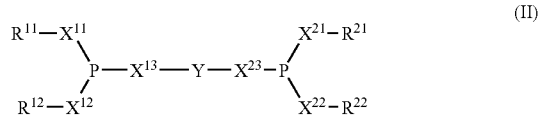

where
$X^{11}$, $X^{12}$, $X^{13}$ $X^{21}$, $X^{22}$, $X^{23}$ are each independently oxygen or a single bond
$R^{11}$, $R^{12}$ are each independently identical or different, separate or bridged organic radicals
$R^{21}$ $R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}$, $X^{12}$, $X^{13}$, $X^{21}$, $X^{22}$, $X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is advantageously an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be the same or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application of reference number DE 103 50 999.2 of Oct. 30, 2003 which has an earlier priority date but had not been published at the priority date of the present application.

The compounds I, Ia, Ib and II described and their preparation are known per se. The phosphorus ligands used may also be mixtures comprising at least two of the compounds I, Ia, Ib and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula Ib

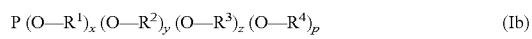

where $R^1$, $R^2$ and $R^3$ are each independently selected from o-isopropylphenyl, m-tolyl and p-tolyl, $R^4$ is phenyl; x is 1 or 2, and y, z, p are each independently 0,1 or 2 with the proviso that x+y+z+p=3; and mixtures thereof.

Reduction

The process according to the invention for preparing nickel (0)-phosphorus ligand complexes containing at least one nickel(0) central atom and at least one phosphorus ligand by reduction is preferably carried out in the presence of a solvent. The solvent is selected in particular from the group consisting of organic nitriles, aromatic hydrocarbons, aliphatic hydrocarbons and mixtures of the aforementioned solvents. With regard to the organic nitriles, preference is given to acetonitrile, propionitrile, n-butyronitrile, n-valeronitrile, cyanocyclopropane, acrylonitrile, crotonitrile, allyl cyanide, cis-2-pentenenitrile, trans-2-pentenenitrile, cis-3-pentenenitrile, trans-3-pentenenitrile, 4-pentenenitrile, 2-methyl-3-butenenitrile, Z-2-methyl-2-butenenitrile, E-2-methyl-2-butenenitrile, ethylsuccinonitrile, adiponitrile, methylglutaronitrile or mixtures thereof. With regard to the aromatic hydrocarbons, benzene, toluene, o-xylene, m-xylene, p-xylene or mixtures thereof may preferably be used. Aliphatic hydrocarbons may preferably be selected from the group of the linear or branched aliphatic hydrocarbons, more preferably from the group of the cycloaliphatics, such as cyclohexane or methylcyclohexane, or mixtures thereof. Particular preference is given to using cis-3-pentenenitrile, trans-3-pentenenitrile, adiponitrile, methylglutaronitrile or mixtures thereof as the solvent.

Preference is given to using an inert solvent.

The concentration of the solvent is preferably from 10 to 90% by mass, more preferably from 20 to 70% by mass, in particular from 30 to 60% by mass, based in each case on the finished reaction mixture.

In a particular embodiment of the present invention, the solvent is identical to the diluent which is used in the above-described process according to the invention for preparing the anhydrous mixture comprising the nickel(II) halide and the diluent.

In the process according to the invention, the concentration of the ligand in the solvent is preferably from 1 to 90% by weight, more preferably from 5 to 80% by weight, in particular from 50 to 80% by weight.

The reducing agent used in the process according to the invention is preferably selected from the group consisting of metals which are more electropositive than nickel, metal alkyls, electrical current, complex hydrides and hydrogen.

When the reducing agent in the process according to the invention is a metal which is more electropositive than nickel, this metal is preferably selected from the group consisting of sodium, lithium, potassium, magnesium, calcium, barium, strontium, titanium, vanadium, iron, cobalt, copper, zinc, cadmium, aluminum, gallium, indium, tin, lead and thorium. Particular preference is given in this context to iron and zinc. When aluminum is used as the reducing agent, it is advantageous when it is preactivated by reaction with a catalytic amount of mercury(II) salt or metal alkyl. Preference is given to using triethylaluminum for the preactivation in an amount of preferably from 0.05 to 50 mol %, more preferably from 0.5 to 10 mol %. The reduction metal is preferably finely divided, the expression "finely divided" meaning that the metal is used in a particle size of less than 10 mesh, more preferably less than 20 mesh.

When the reducing agent used in the process according to the invention is a metal which is more electropositive than nickel, the amount of metal is preferably from 0.1 to 50% by weight, based on the reaction mixture.

When metal alkyls are used as reducing agents in the process according to the invention, they are preferably lithium alkyls, sodium alkyls, magnesium alkyls, in particular Grignard reagents, zinc alkyls or aluminum alkyls. Particular preference is given to aluminum alkyls such as trimethylaluminum, triethylaluminum, triiso-propylaluminum or mixtures thereof, in particular triethylaluminum. The metal alkyls may be used without solvent or dissolved in an inert organic solvent such as hexane, heptane or toluene.

When complex hydrides are used as the reducing agent in the process according to the invention, preference is given to using metal aluminum hydrides such as lithium aluminum hydride, or metal borohydrides such as sodium borohydride.

The molar ratio of redox equivalents between the nickel(II) source and the reducing agent is preferably from 1:1 to 1:100, more preferably from 1:1 to 1:50, in particular from 1:1 to 1:5.

In the process according to-the invention, the ligand to be used may also be present in a ligand solution which has already been used as a catalyst solution in hydrocyanation reactions and which is depleted of nickel(0). This residual catalyst solution generally has the following composition:

from 2 to 60% by weight, in particular from 10 to 40% by weight, of pentenenitriles, from 0 to 60% by weight, in particular from 0 to 40% by weight, of adiponitrile, from 0 to 10% by weight, in particular from 0 to 5% by weight, of other nitriles, from 10 to 90% by weight, in particular from 50 to 90% by weight, of phosphorus ligand and from 0 to 2% by weight, in particular from 0 to 1% by weight, of nickel(0).

In the process according to the invention, the free ligand present in the residual catalyst solution may thus be converted back to a nickel(0) complex.

In a particular embodiment of the present invention, the ratio of the nickel(III) source to phosphorus ligand is from 1:1 to 1:100. Further preferred ratios of nickel(II) source to phosphorus ligand are from 1:1 to 1:3, in particular from 1:1 to 1:2.

The process according to the invention may be carried out at any pressure. For practical reasons, preference is given to pressures between 0.1 bar abs and 5 bar abs, preferably 0.5 bar abs and 1.5 bar abs.

The process according to the invention may be carried out in batch mode or continuously.

It is possible to use the nickel(I)-ether adduct directly in the solution or suspension obtained in this way to prepare the nickel(0)-phosphorus ligand complexes. Alternatively, the adduct may also initially be isolated and optionally dried, and be dissolved again or resuspended to prepare the nickel(0)-phosphorus ligand complex. The adduct can be isolated from the suspension by processes known per se to those skilled in the art such as filtration, centrifugation, sedimentation or by hydrocyclones, as described, for example, in Ullmann's Encyclopedia of Industrial Chemistry, Unit Operation I, Vol. B2, VCH, Weinheim, 1988, in chapter 10, pages 10-1 to 10-59, chapter 11, pages 11-1 to 11-27 and chapter 12, pages 12-1 to 12-61.

In the process according to the invention, it is possible to work without excess of nickel(II) halide or reducing agent, for example zinc, so that there is no need to remove them after the nickel(0) complex formation.

In a particular embodiment of the present invention, the process according to the invention comprises the following process steps:

(1) drying an aqueous nickel(II) halide by azeotropic distillation, (2) precomplexing the azeotropically dried nickel(II) halide in a solvent in the presence of a phosphorus ligand, (3) adding at least one reducing agent at an addition temperature of from 20 to 120° C. to the solution or suspension stemming from process step (2), (4) stirring the suspension or solution stemming from process step (3) at a reaction temperature of from 20 to 120° C.

The precomplexation temperatures, addition temperatures, and reaction temperatures may each independently be from 20° C. to 120° C. In the precomplexation, addition and reaction, particular preference is given to temperatures of from 30° C. to 80° C.

The precomplexation periods, addition periods and reaction periods may each independently be from 1 minute to 24 hours. The precomplexation period is in particular from 1 minute to 3 hours. The addition period is preferably from 1 minute to 30 minutes. The reaction period is preferably from 20 minutes to 5 hours.

The present invention further provides the solutions comprising nickel(0)-phosphorus ligand complexes obtainable by the process according to the invention, and also their use in the hydrocyanation of alkenes and of unsaturated nitriles, in particular in the hydrocyanation of butadiene to prepare a mixture of pentenenitriles and the hydrocyanation of pentenenitriles to adiponitrile. The present invention also relates to their use in the isomerization of alkenes and of unsaturated nitriles, in particular of 2-methyl-3-butenenitrile to 3-pentenenitrile.

The present invention further provides a process for preparing a nickel(II) halide dried by azeotropic distillation, by removing water from mixtures comprising at least one aqueous nickel(II) halide, by admixing the mixture with a diluent whose boiling point, in the case that the diluent mentioned does not form an azeotrope with water under the pressure conditions of the distillation mentioned below, is higher than the boiling point of water and is liquid at this boiling point of water, or which forms an azeotrope or heteroazeotrope with water under the pressure and temperature conditions of the distillation mentioned below, and distilling the mixture comprising the aqueous nickel(II) halide and the diluent to remove water or the azeotrope mentioned or the heteroazeotrope mentioned from this mixture to obtain an anhydrous mixture comprising nickel(II) halide and said diluent. Further embodiments and configurations of this process have already been described above.

The present inventions are illustrated in detail by the examples which follow.

EXAMPLES

In the examples of complex synthesis, the chelate ligand solution used was a solution of the chelate phosphonite 1

1

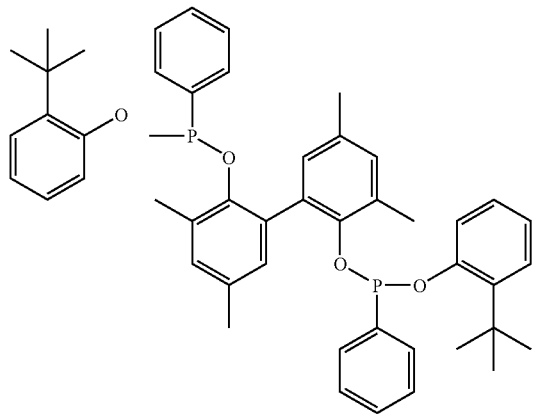

in 3-pentenenitrile (65% by weight of chelate, 35% by weight of 3-pentenenitrile).

To determine the conversion, the complex solutions prepared were investigated for their content of active, complexed Ni(0). To this end, the solutions were admixed with tri(m/p-tolyl) phosphite (typically 1 g of phosphite per 1 g of solution) and kept at 80° C. for approx. 30 min, in order to achieve complete transcomplexation. Subsequently, the current-voltage curve for the electrochemical oxidation was determined in a cyclic voltammetry measurement apparatus in unstirred solution against a reference electrode, which provides the peak current which is proportional to the concentration and determines, via calibration with solutions of known Ni(0) concentrations, the Ni(0) content of the test solutions, corrected by the subsequent dilution with tri(m/p-tolyl) phosphite. The Ni(0) values quoted in the examples report the content of Ni(0) in % by weight based on the entire reaction solution, determined by this method.

Examples 1-4 describe the preparation of the suspensions with directly following complex formation:

Example 1

In a 250 ml flask equipped with stirrer and water separator, of 9.7 g of NiCl$_2$.6H$_2$O (41 mmol) were suspended in 100 ml of 3-pentenenitrile. The mixture was heated to boiling under reflux and the water thus separated out. This gave a fine suspension in 3-pentenenitrile. The suspension was concentrated almost to dryness, resuspended in 13 g of 3-pentenenitrile and admixed with 100 g of chelate solution (86 mmol of ligand). At 50° C., 4 g of Zn powder (61 mmol, 1.4 eq.) were added, and the mixture was heated to 60° C. and stirred for 3 h. Since no conversion was observed, stirring was continued at 80° C. for another 3 h. An Ni(0) value of 1.1% (56% conversion) was measured.

Example 2

In a 500 ml flask equipped with stirrer and water separator, a solution of 9.7 g of NiCl$_2$.6H$_2$O (41 mmol) in 10 g of water was admixed with 150 g of 3-pentenenitrile. The biphasic mixture was heated to boiling under reflux and the water thus separated out. This gave a fine suspension in 3-pentenenitrile. The suspension was concentrated almost to dryness, resuspended in 13 g of 3-pentenenitrile and admixed with 100 g of chelate solution (86 mmol of ligand). At 80° C., 4 g of Zn powder (61 mmol, 1.4 eq.) were added, and the mixture was stirred for 6 h. An Ni(0) value of 1.4% (71% conversion) was measured.

Example 3

A suspension prepared in a similar manner to example 2 was concentrated almost to dryness, resuspended in 3 9 of 3-pentenenitrile and admixed with 50 g of chelate solution (43 mmol of ligand). At 80° C., 4 g of Zn powder (61 mmol, 1.4 eq.) were added and the mixture was stirred for 4 h. An Ni(0) value of 2.3% (60% conversion) was measured.

Example 4

In a 250 ml flask equipped with stirrer and water separator, a solution of 19.7 g of NiCl2.6H$_2$O (83 mmol) in 20 g of water was admixed with 61 g of 3-pentenenitrile. The biphasic mixture was heated to boiling under reflux and the water thus separated out. This gave a thick suspension in 3-pentenenitrile which was still just stirrable. After cooling to 80° C., it suspension was admixed with 100 g of chelate solution (86 mmol of ligand). Subsequently, 8 g of Zn powder (122 mmol, 1.4 eq.) were added at 80° C. and the mixture was stirred for 4 h. An Ni(0) value of 1.2% (45% conversion) was measured.

Examples 5 and 6 describe the separate preparation of an NiCl$_2$ suspension.

Example 5

In a 2 l flask equipped with stirrer and water separator, a solution of 194 g of NiCl$_2$.6H$_2$O (816 mmol) in 100 g of water was admixed with 300 g of 3-pentenenitrile. The biphasic mixture was heated to boiling under reflux and the water thus separated out. Once 161 g of water (86% of the theoretical amount) had been removed, parts of the suspension had become so viscous and parts had solidified to form large solid agglomerates that the experiment had to be terminated.

Example 6

In a 2 l flask equipped with stirrer, water separator and dropping funnel, 700 g of 3-pentenenitrile was heated to boiling under reflux. A solution of 194 g of NiCl$_2$.6H$_2$O (816 mmol) in 105 g of water was added dropwise to this boiling pentenenitrile at just the rate at which the water was removed again in the water separator. This gave a fine, almost homogenous suspension in 3-pentenenitrile.

Examples 7-12 describe the preparation of the nickel complexes from a separately prepared suspension.

Example 7

In a 500 ml flask equipped with stirrer, 74 g of a suspension prepared according to example 6 (83 mmol of $NiCl_2$) were admixed under argon with 100 g of chelate solution (86 mmol of ligand) and stirred at 80° C. for 15 min. Subsequently, 8 g of Zn powder (122 mmol, 1.5 eq.) were added at 80° C. and the mixture was stirred at 80° C. for 5 h. An Ni(0) value of 1.7% (64% conversion) was measured.

Example 8

In a 250 ml flask equipped with stirrer, 37 g of a suspension prepared according to example 6 (42 mmol of $NiCl_2$) were admixed under argon with 50 g of chelate solution (43 mmol of ligand) and stirred at 50° C. for 15 min. Subsequently, 3 g of Zn powder (46 mmol, 1.1 eq.) were added at 50° C. and the mixture was stirred at 50° C. for 5 h. An Ni(0) value of 1.2% (43% conversion) was measured.

Example 9

A reaction was carried out in a similar manner to example 8, except that the mixture was heated to 80° C. before Zn powder was added. After 5 h, an Ni(0) value of 1.4% (50% conversion) was measured.

Example 10

A reaction was carried out in a similar manner to example 8, except that all steps were carried out at 80° C. After 5 h, an Ni(0) value of 1.8% (61% conversion) was measured.

Example 11

A reaction was carried out in a similar manner to example 7, except that 6.8 g of Fe powder (122 mmol, 1.5 eq.) were added instead of Zn powder. After 5 h, an Ni(0) value of 1.2% (53% conversion) was measured.

Example 12

In a 250 ml flask equipped with stirrer, 47.6 g of a suspension prepared according to example 6 (53 mmol of $NiCl_2$) were suspended under argon in 67.3 g of chelate solution (58 mmol of ligand) and cooled to 0° C. Subsequently, 26.5 g of a 25% solution of triethylaluminum in toluene (58 mmol) were slowly metered in. After the solution had been warmed to room temperature, it was stirred for a further 10 h. An Ni(0) value of 0.64% (28% conversion) was measured.

In example 13, the ligand solution used was "residual catalyst solution" which had already been used as the catalyst solution in hydrocyanation reactions and had been strongly depleted in Ni(0). The composition of the solution is approx. 20% by weight of pentenenitriles, approx. 6% by weight of adiponitrile, approx. 3% by weight of other nitriles, approx. 70% by weight of ligand (consisting of a mixture of 40 mol % of chelate phosphonite 1 and 60 mol% of tri((m/p-tolyl) phosphite) and a nickel(0) content of only 0.8% by weight.

Example 13

In a 250 ml flask equipped with stirrer, 37 g of a suspension prepared according to example 6 (42 mmol of $NiCl_2$) were admixed under argon with 50 g of residual catalyst solution and stirred at 80° C. for 15 min. Subsequently, 3 g of Zn powder (46 mmol, 1.1 eq.) were added at 80° C. and the mixture was stirred at 80° C. for 5 h. An Ni(0) value of 1.64% (corresponding to a P:Ni ratio of 4:1) was measured.

In examples 14 to 19, the ligand used was tri(m/p-tolyl phosphite).

Example 14

In a 250 ml flask equipped with stirrer, 100 g of a suspension prepared in a similar manner to example 6 (25 mmol of $NiCl_2$) were admixed under argon with 36 g (100 mmol) of tri(m/p-tolyl) phosphite and stirred at 80° C. for 5 min. Subsequently, 1.8 g of Zn powder (28 mmol, 1.1 eq.) were added at 80° C. and the mixture was stirred at 80° C. for 4 h. An Ni(0) value of 0.75% (72% conversion) was measured.

Example 15

A reaction was carried out in a similar manner to example 14, except that 53.8 g (152 mmol) of tri(m/p-tolyl) phosphite were used. An Ni(0) value of 0.8% (85% conversion) was measured.

Example 16

A reaction was carried out in a similar manner to example 15 except that all process stages were carried out at 40° C. An Ni(0) value of 0.6% (65% conversion) was measured.

Example 17

A reaction was carried out in a similar manner to example 15 except that all process stages were carried out at 60° C. An Ni(0) value of 0.95% (99% conversion) was measured.

Example 18

A reaction was carried out in a similar manner to example 14, except that 71.8 g (203 mmol) of tri(m/p-tolyl) phosphite were used. An Ni(0) value of 0.5% (85% conversion) was measured.

In the comparative examples, commercially available, anhydrous nickel chloride was b used as the nickel source:

Comparative Example 1

In a 500 ml flask with stirrer, 11 g (85 mmol) of $NiCl_2$ were suspended under argon in 13 g of 3-pentenenitrile, admixed with 100 g of chelate solution (86 mmol of ligand) and stirred at 80° C. for 15 min. After cooling to 40° C., 8 g of Zn powder (122 mmol, 1.4 eq.) were added and the mixture was stirred at 40° C. for 4 h. An Ni(0) value of 0.05% (1% conversion) was measured.

Comparative Example 2

A reaction was carried out in a similar manner to Comparative example 1, except that the temperature was kept at 80° C. when the Zn powder was added. After 5 h, an Ni(0) value of 0.4% (10% conversion) was measured.

Comparative Example 3

In a 500 ml flask with stirrer, 11 g (85 mmol) of $NiCl_2$ were suspended under argon in 13 g of 3-pentenenitrile, admixed with 100 g of chelate solution (86 mmol of ligand) and stirred at 80° C. for 15 min. After cooling to 60° C., 5.3 g of Zn powder (95 mmol, 1.1 eq.) were added and the mixture was stirred at 60-65° C. for 10 h. An Ni(0) value of 0.16% (4% conversion) was measured.

Comparative Example 4

A reaction was carried out in a similar manner to Comparative example 3, except that the temperature was kept at 80° C. when the Fe powder was added. After 10 h, an Ni(0) value of 0.4% (10% conversion) was measured.

We claim:

1. A process for preparing a nickel(0)-phosphorus ligand complex containing at least one nickel(0) central atom and at least one phosphorus ligand, which comprises reducing a nickel(II) halide dried by azeotropic distillation in the presence of a reducing agent and at least one bidentate phosphorus ligand selected from the group consisting of phosphites, phosphinites and phosphonites.

2. The process according to claim 1, wherein the nickel(II) halides are selected from the group consisting of nickel(II) chloride, nickel(II) bromide and nickel(II) iodide.

3. The process according to claim 1, wherein the nickel(II)-halide dried by azeotropic distillation is obtained by adding a diluent whose boiling point, in the case that the diluent mentioned does not form an azeotrope with water under the pressure conditions of the distillation, is higher than the boiling point of water and is liquid at this boiling point of water, or which forms an azeotrope or heteroazeotrope with water under the pressure and temperature conditions of the distillation, to an aqueous nickel(II) halide to form a mixture, and distilling the mixture comprising the aqueous nickel(II) halide and the diluent to remove the water, the azeotrope or the heteroazeotrope from the mixture to obtain an anhydrous mixture comprising nickel(II) halide and said diluent.

4. The process according to claim 3, wherein the diluent is an organic nitrile.

5. The process according to claim 1, wherein the reducing agent is a metal which is more electropositive than nickel.

6. The process according to claim 1, wherein the reducing agent is a metal allyl, electrical current, a complex hydride or hydrogen.

7. The process according to claim 1, wherein the phosphorus ligand is provided by a catalyst solution which was used in hydrocyanation reactions.

8. The process according to claim 3, wherein the reducing agent is a metal which is more electropositive than nickel.

9. The process according to claim 3, wherein the diluent is selected from the group consisting of organic nitriles, aromatic hydrocarbons and mixtures thereof.

10. The process according to claim 3, wherein the diluent is an organic nitrile or is a mixture of two or more diluents comprising at least one organic nitrile, said organic nitrile selected from the group consisting of cis-3-pentenenitrile, trans-3-pentenenitrile, adiponitrile, methylglutaronitrile and mixtures thereof.

* * * * *